US006949076B1

(12) United States Patent
Kevala

(10) Patent No.: US 6,949,076 B1
(45) Date of Patent: Sep. 27, 2005

(54) PORTABLE LOWER BACK SUPPORT

(76) Inventor: Ruby K. Kevala, 7575 Wilson St., Ventura, CA (US) 93003

( * ) Notice: Subject to any disclaimer, the term of this patent is extended or adjusted under 35 U.S.C. 154(b) by 248 days.

(21) Appl. No.: 10/326,951

(22) Filed: Dec. 23, 2002

(51) Int. Cl.⁷ .............................................. A61F 5/00
(52) U.S. Cl. ....................................... 602/19; 128/876
(58) Field of Search ............................... 128/845, 846, 128/869–874; 602/5, 19; 450/94, 115–117, 450/119, 121–125

(56) References Cited

U.S. PATENT DOCUMENTS

| 2,554,337 A | * | 5/1951 | Lampert ..................... 606/237 |
| 5,634,891 A | * | 6/1997 | Beczak, Sr. et al. .......... 602/19 |
| 6,666,838 B2 | * | 12/2003 | Modglin et al. .............. 602/19 |

* cited by examiner

Primary Examiner—Michael A. Brown
(74) Attorney, Agent, or Firm—Albert O. Cota

(57) ABSTRACT

A portable lower back support (10) having a center section (12), a right articulated section (28) and a left articulated section (44). Both the right (28) and the left (44) articulated sections are attached to each respective side of the center section (12) by an attachment means (66,70) that typically comprises a utility hinge (74). Extending across the front of the right articulated section (28), the center section (12) and the left articulated section (44) is a horizontal front support (82). Extending from the top to the bottom of the center section (12) is a vertical front support (98). Both the horizontal and the vertical front supports (82,98) provide the necessary support for a person's lower back while using the back support (10). Extending across the back of the right and left articulated sections (20,42) and the center section (12) is a horizontal rear strap (114) which maintains the back support (10) in an "open" position, or allows the back support (10) to be folded flat for transportation and storage.

22 Claims, 5 Drawing Sheets

US 6,949,076 B1

PORTABLE LOWER BACK SUPPORT

TECHNICAL FIELD

The invention pertains to the general field of back supports and more particularly to a portable lower back support that utilizes straps for the required back support and that can be folded to facilitate transportation and storage.

BACKGROUND ART

Studies have shown that humans spend a significant amount of their lives in a seated position. This is a result of many occupations and educational pursuits requiring a person to utilize a desk. Sitting is also a favored position for relaxation. Unfortunately, a seated position is not usually conducive to proper alignment of a person's back, and moderate to serious damage can occur, especially in the lower back, or lumbar region.

One of the most effective ways to decrease the potential for back damage is for a person to follow the old adage "sit up straight". While sitting up straight is the preferred position for a person seated in a chair, it is often un-comfortable and difficult to maintain for extended periods.

There have been many attempts to remedy this problem. Chairs have been designed that force a person to maintain an up-right sitting position, pads and cushions can be placed on a chair to alter the seating position, and other similar methods have been employed with limited success. One of the few effective means of alleviating this problem is for a person to utilize a device commonly known as a back or lumbar support. A back or lumbar support, as the name implies, provides additional support to a person's lower back region while sitting. Back or lumbar supports are designed in many different ways. There are belts that a person wears, which are similar to weight-lifter's belts, there are L-shaped or circular cushions that are placed on a chair's seat or against a chair's back, and, especially popular with automobile designers, there are internal back support devices that are built into a vehicle seat that can be activated and adjusted as needed.

While some of these devices/methods are more effective than others, they all provide some degree of additional lower back support. One of the drawbacks to many of the most effective supports is that they can only be used on a single chair, such as the internal type, or even though they are not usually large, it is often difficult to transport them and/or use a certain lumbar support with a wide variety of chairs.

Obviously, if there were a lumbar support that was truly portable, that could be transported and stored with ease and that functioned well with many different types of chairs, it would be very beneficial for a large number of people.

A search of the prior art did not disclose any literature or patents that read directly on the claims of the instant invention. However, the following U.S. patents are considered related:

| U.S. PAT. NO. | INVENTOR | ISSUED |
| --- | --- | --- |
| 5,954,399 | Hong | Sep. 21, 1999 |
| 5,413,262 | Dewire, et al | May 9, 1995 |
| 5,363,863 | Lelli, et al | Nov. 15, 1994 |

The U.S. Pat. No. 5,954,399 patent discloses a lumbar support designed to be placed against the back support of a vehicle seat. The support includes a wire frame that is attached to the back of the vehicle seat by means of two vertical members. One of the vertical members includes an adjusting knob that sets the tension of the wire frame. Below the wire frame is located a lower back strap that is also attached to the two vertical members. The lower back strap can also be adjusted for tension by means of the adjusting knob.

The U.S. Pat. No. 5,413,262 patent discloses a lumbar supporting belt which includes a wide inner belt and a relatively narrow outer belt. The inner belt extends about the waist of a person and has a middle region that is positioned in the lumbar region of the back. The inner belt is formed of a soft, flexible material which has opposing ends that are releasably connected. The outer belt extends about the waist of a person, overlies the inner belt and has opposing ends corresponding to the opposing ends of the inner belt which are adapted to be placed in proximity to one another. The outer belt is formed of a flexible, non-stretchable material which has opposing ends releasably connected.

The U.S. Pat. No. 5,363,863 patent discloses a lumbar support belt. The belt includes a rear lumbar support piece, a front abdominal support piece, two lateral hip support pieces and a length adjustment means.

For background purposes and as indicative of the art to which the invention relates, reference may be made to the following remaining patents found in the search:

| U.S. PAT. NO. | INVENTOR | ISSUED |
| --- | --- | --- |
| 6,270,158 | Hong | Aug. 7, 2001 |
| 5,567,010 | Sparks | Oct. 22, 1996 |
| 5,254,065 | Pollock | Oct. 19, 1993 |
| 4,832,400 | Aoki, et al | May 23, 1989 |
| 4,313,637 | Barley | Feb. 2, 1982 |

DISCLOSURE OF THE INVENTION

The portable lower back support disclosed herein is adapted to be placed upon a chair's sitting surface, adjacent the chair back's lower section to provide additional lower back support for a person sitting on the chair.

The portable lower back support typically comprises a center section, a right articulated section and a left articulated section. All three sections are preferably made of high-impact plastic; however, a metal, such as aluminum or wood can also be utilized. The right articulated section and the left articulated section are each respectively attached, by an attachment means to one side of the center section. The attachment means are hinges, which can be comprised of utility hinges, piano hinges or living hinges.

Extending across the front of the right articulated section, the center section and the left articulated section is a horizontal front support that typically consists of at least one fabric strap. Extending from the top to the bottom of the center section is a vertical front support that also consists of at least one fabric strap. Both the horizontal and the vertical front support are utilized to provide the increased support for a person's lower back when using the portable lower back support.

Extending across the back of the right articulated section, the center section and the left articulated section is a horizontal rear strap. The rear strap is removably attached to the right and left articulated sections, or a buckle is located on the rear strap. Whenever the horizontal rear strap is tightly in place, the portable lower back support is maintained in an "open" position, with the right and left articulated sections angularly extended. Once either of the horizontal rear strap's ends are removed, or the buckle is unclasped, the right and left articulated sections can be folded inward to create a flat structure, which is easy to transport and store.

In view of the above disclosure, the primary object of the invention is to provide a portable lower back support that can significantly improve lower back support for a person sitting on a chair and that can be folded flat for transportation and storage.

It is also an object to provide a portable lower back support that:

o can be placed on various types of chairs,
o can be made in various colors and of various materials,
o is virtually maintenance free,
o can be dimensioned to accommodate the stature of various persons,
o does not interfere with a vehicle seat belt or shoulder harness,
o can be made with a vertical length that supports only the lower back or the vertical length can be extended to support the entire back, and
o is cost effective from both a manufacturer's and consumer's point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
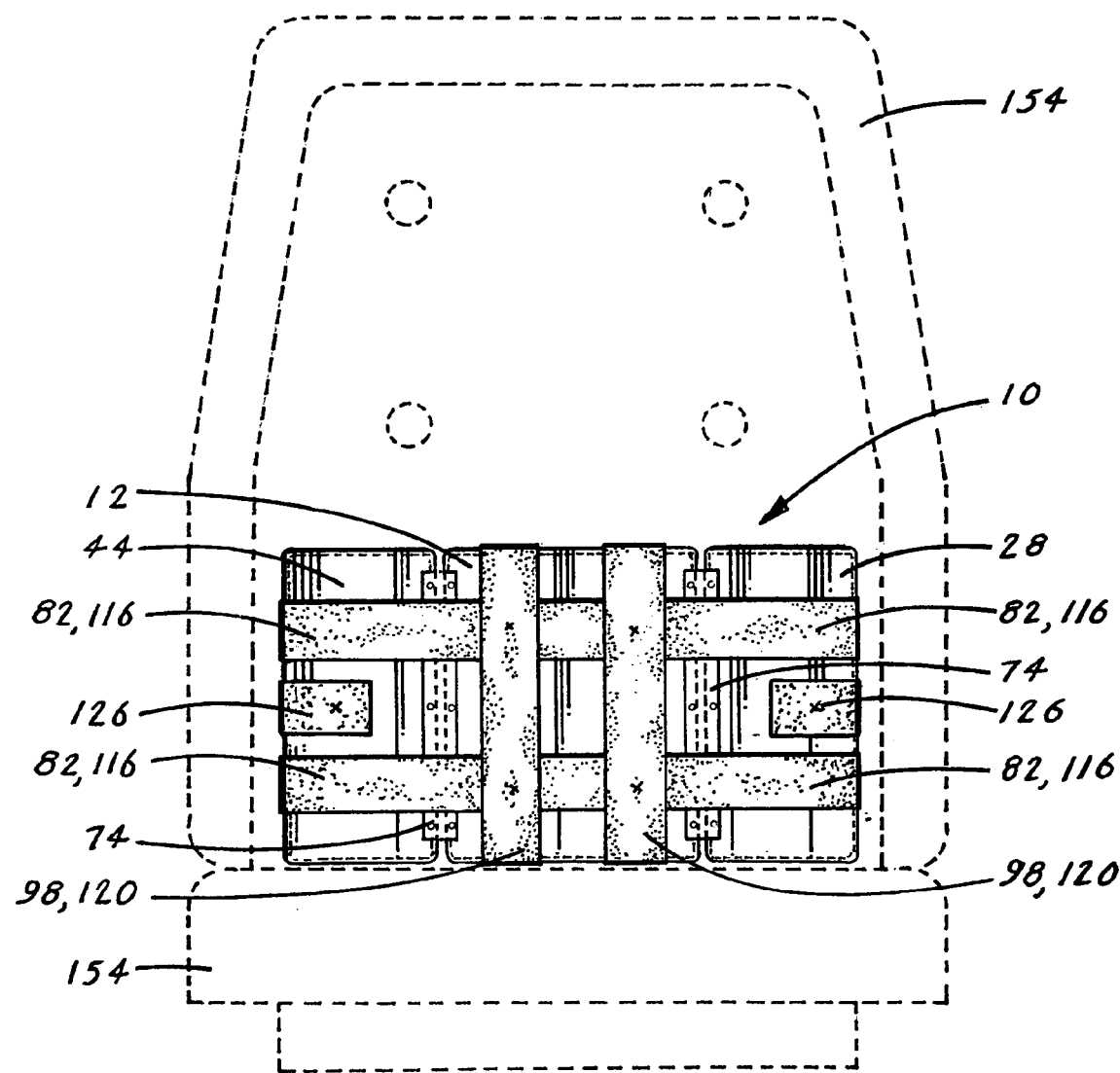
FIG. 1 is a front elevational view of a portable lower back support shown in its extended functional configuration and placed upon a chair seat which is shown with broken lines and is not an element of the claimed invention.

The best mode for carrying out the invention is presented in terms of a preferred embodiment for a portable lower back support 10, (hereinafter "PLBS 10)". The PLBS 10 is designed to be placed upon the seating surface of a chair 154, near the lower section of the chair's back. Whenever a person sits on a chair with the PLBS 10 in place, a significantly greater amount of lower back support is provided.

As shown in FIGS. 1–7, the PLBS 10 is comprised of the following major elements: a center section 12, a right articulated section 28, a left articulated section 44, a horizontal front support 82, a vertical front support 98 and a horizontal rear strap 126.

Figure 2:
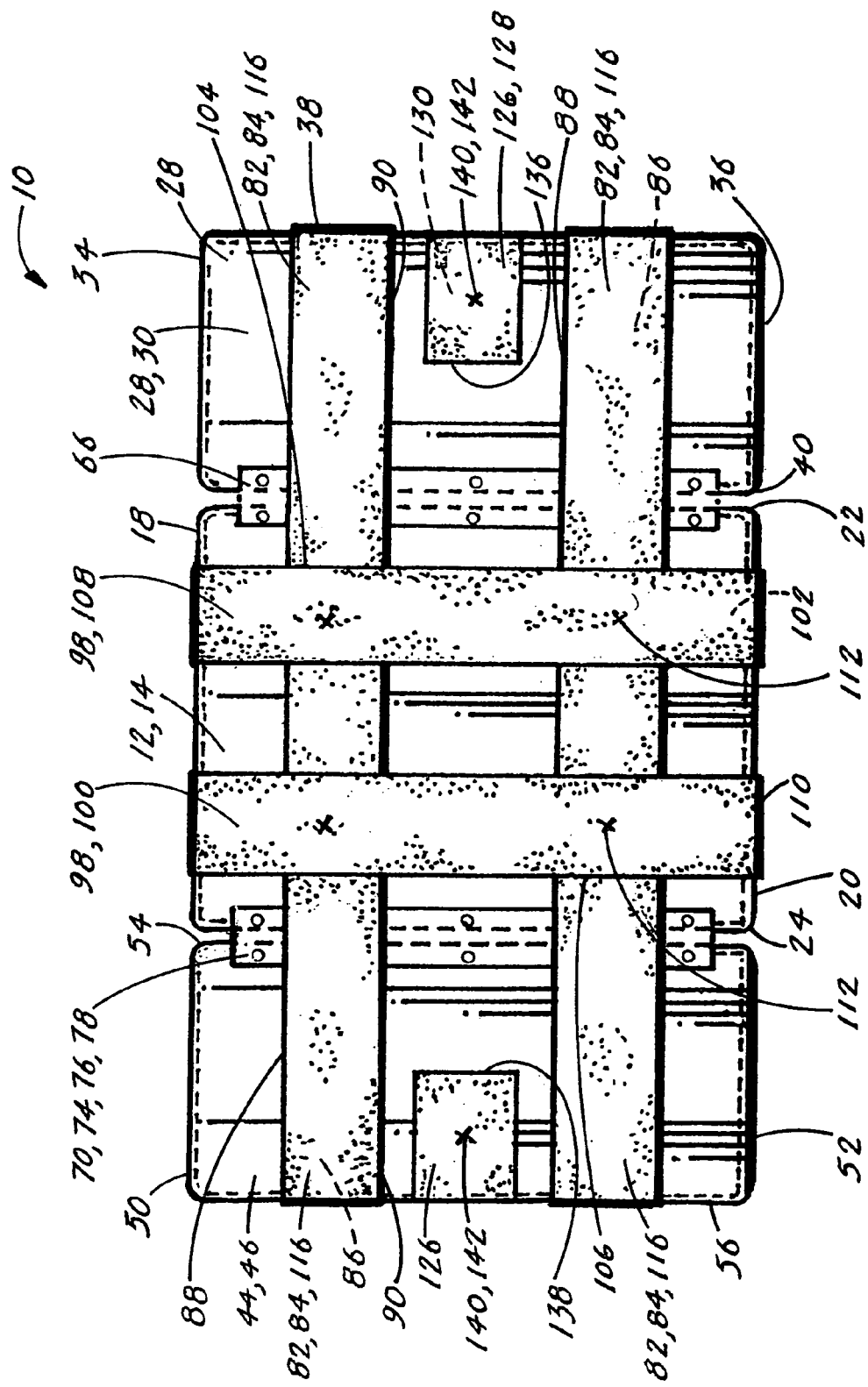
FIG. 2 is a front elevational view of the portable lower back support.
Figure 3:
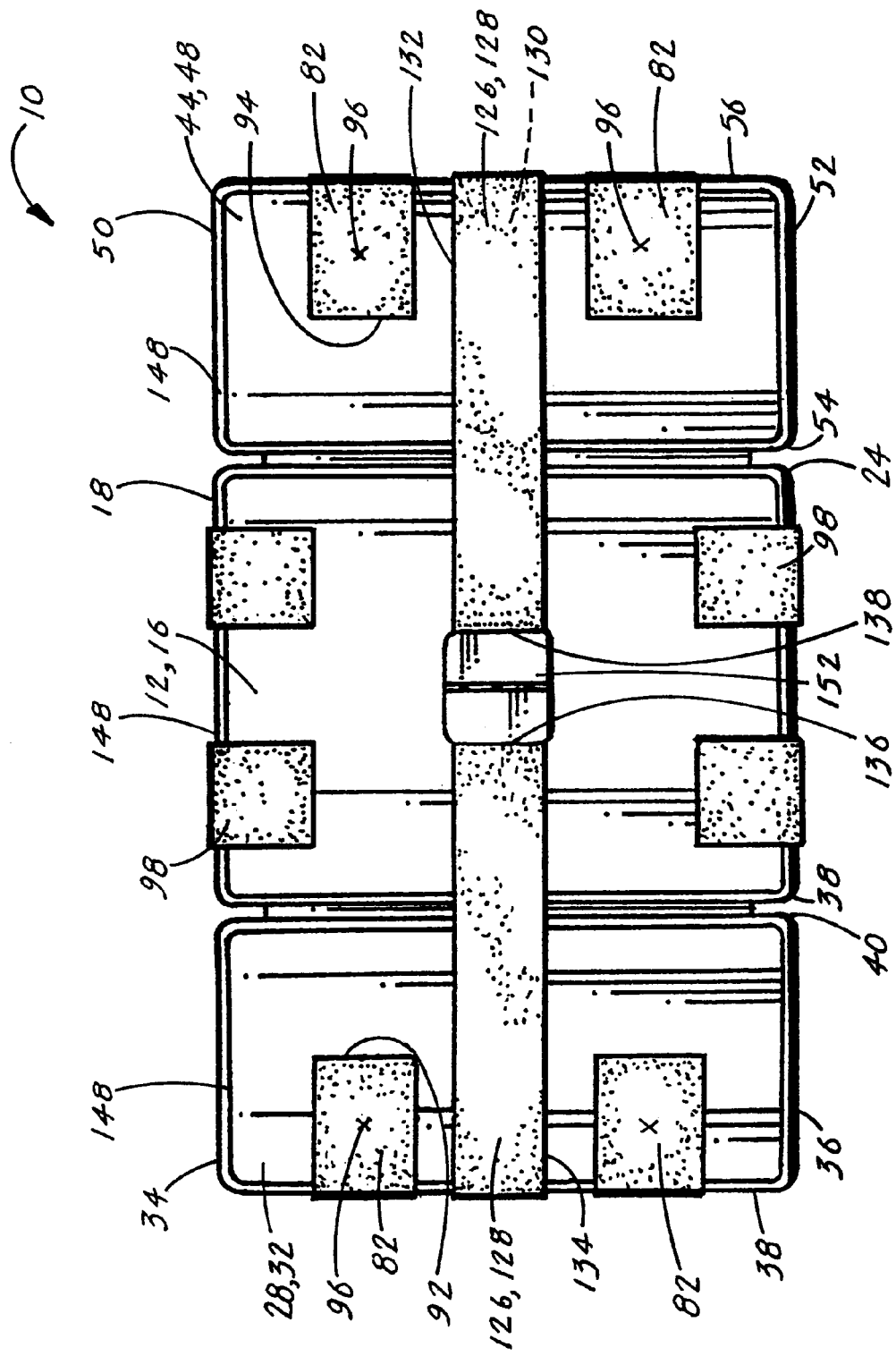
FIG. 3 is a rear elevational view of the portable lower back support shown with a horizontal rear strap that includes a buckle.
Figure 4:
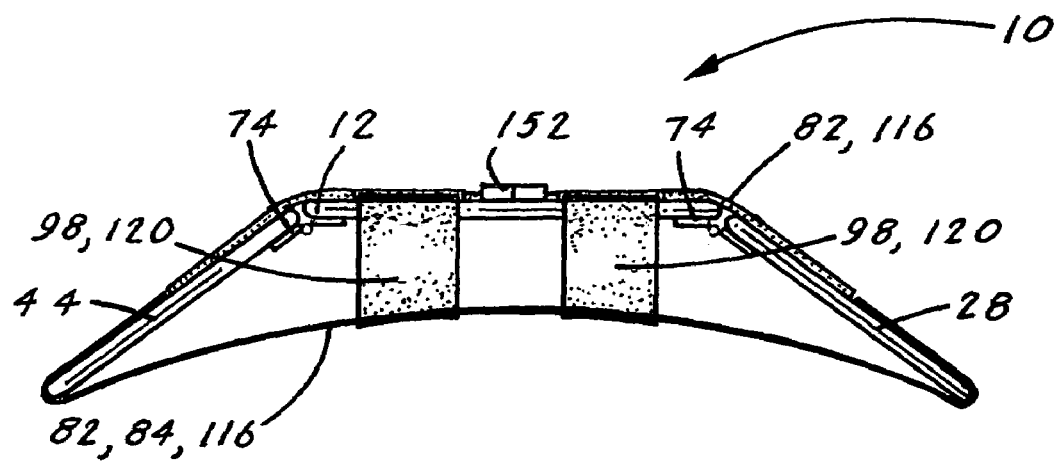
FIG. 4 is a top plan view of the portable lower back support.
Figure 5:
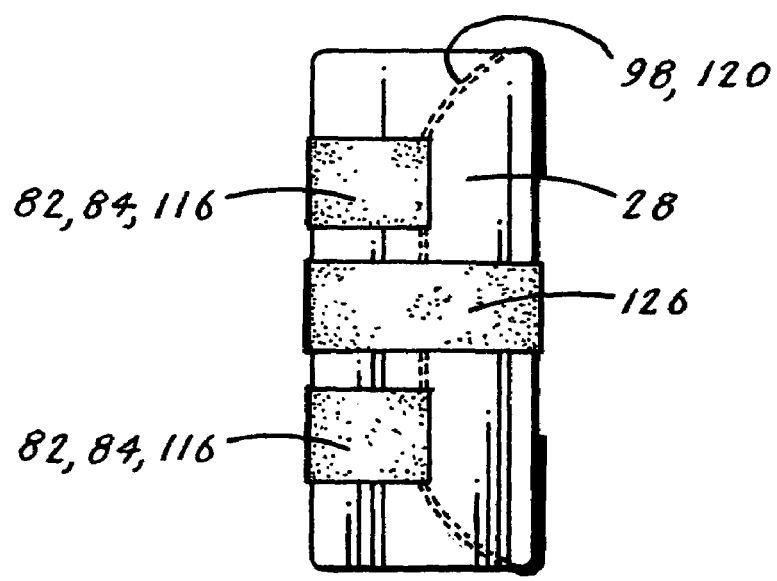
FIG. 5 is a left right elevational view the right side elevational view being a mirror image.

As shown best in FIGS. 2–3, the center section 12 is comprised of a front surface 14, a rear surface 16, an upper edge 18, a lower edge 20, a right edge 22 and a left edge 24. The right articulated section 28, also shown best in FIGS. 2–3, is comprised of a front surface 30, a rear surface 32, an upper edge 34, a lower edge 36, a right edge 38 and a left edge 40. The left articulated section 44, as also shown best in FIGS. 2–3, is essentially a mirror image of the right articulated section 28. The left section 44 also has a front surface 46, a rear surface 48, an upper edge 50, a lower edge 52, a right edge 54 and a left edge 56. All three sections: the center, the right articulated and the left articulated are preferably made of a high-impact plastic. Additionally, a metal such as aluminum or wood can also be utilized.

As shown in FIGS. 1–4, the right articulated section's left edge 40 is attached, by an attachment means 66, to the center section's right edge 22. The left articulated section's right edge 54 is also attached by an attachment means 70 to the center section's left edge 24. The attachment means 66 and 70 are comprised of either a single utility hinge 74, piano hinge 76 or a living hinge 78, or at least two utility hinges 74 or living hinges 78.

As shown in FIGS. 1, 2 and 3, the center section 12 and the right and left articulated sections 28,44, when they are made of plastic or metal have a perimeter flange 148 that provides additional structural integrity.

Extending horizontally across the front surfaces of the center section 12 and the right and left articulated sections 28,44 is a horizontal front support 82, as shown best in FIGS. 1–3. The horizontal front support 82 is comprised of a front surface 84, a rear surface 86, an upper edge 88, a lower edge 90, a first end 92 and a second end 94.

Extending vertically from top to bottom across the center section 12 is a vertical front support 98 as also shown in FIGS. 1–3. The vertical front support 98 is also comprised of a front surface 100, a rear surface 102, a right edge 104, a left edge 106, a first (upper) end 108 and a second (lower) end 110.

As shown in FIGS. 1–3, the horizontal front support's first end 92 is attached, by an attachment means 96, to the right articulated section's rear surface 32, and the second end 94 is attached by the attachment means 96 to the left articulated section's rear surface 48. Both the vertical front support's first (upper) end 108 and second (lower) end 110 are attached to the center section's rear surface 16. The attachment means that is utilized to attach the horizontal front support's first and second ends 92,94 and the vertical front support's first and second ends 108,110 can be comprised of an adhesive, such as glue, complimentary snaps, rivets, or hook and loop fasteners.

The horizontal front support 82 can be comprised of a single, wide horizontal front strap (not shown) or a pair of spaced-apart horizontal front straps 116 as shown in the figures. The single strap typically has a width of 6-inches and each of spaced-apart straps have a width of 2-inches. In the same manner, the vertical front support 98 can also be comprised of a single, wide vertical front strap (not shown), having a width of 6-inches, or a pair of 2-inches wide vertical front straps 120 as shown in the figures.

As shown in FIGS. 1–3, a horizontal rear strap 126 is utilized to maintain the right articulated section 28 and the left articulated section 44 in an "open", extended angular position. The horizontal rear strap 126 is comprised of a front surface 128, a rear surface 130, an upper edge 132, a lower edge 134, a first end 136 and a second end 138. The rear straps' first end 136 and second end 138 are respectively attached by an attachment means 140 to the front surface 30 of the right articulated section 28, and the front surface 46 of the left articulated section 44. Whenever the single, wide horizontal front strap 82 is utilized, a pair of slits are cut into the front strap 82 near each end to allow the horizontal rear strap 126 to pass through. As shown in FIGS. 1–3, the pair of horizontal front straps 82 are attached to the pair of vertical straps 120 by an attachment means 112 such as an adhesive, complimentary snaps, stapling, rivets, staples, or hook and loop fasteners.

The attachment means 140 that are used allow the horizontal rear strap 126 to be attached and detached, preferably comprised a hook and loop fastener 142, which is commonly known as VELCRO®.

Additionally, as shown in FIG. 3, the horizontal rear strap 126 can further comprise a buckle 152, which is preferably located where the rear strap 126 crosses over the rear surface 16 of the center section 12. When the buckle 152 is utilized, the two ends 136,138 of the rear strap 126 can be permanently attached to each respective front surface of the right and left articulated sections. The buckle can be comprised of a slide release buckle, a cam release buckle or the like.

Figure 6:
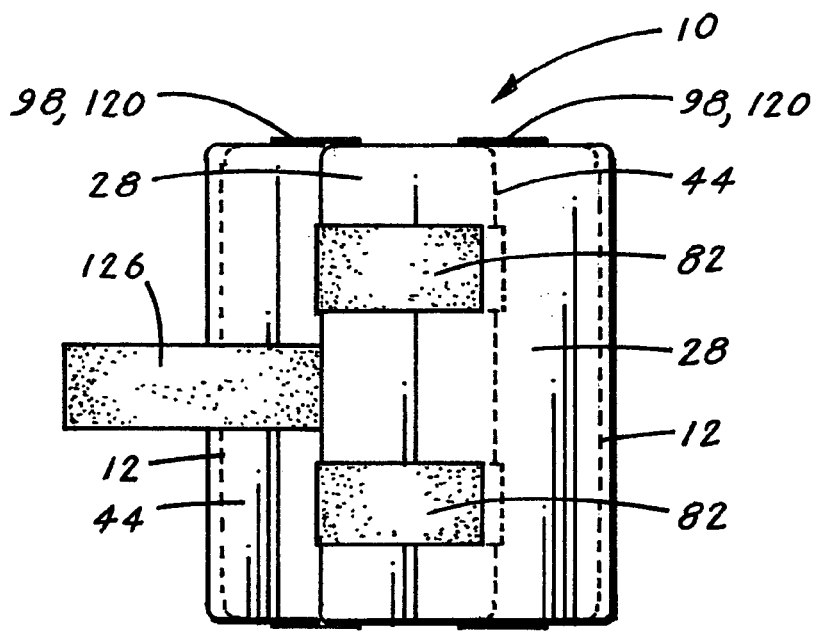
FIG. 6 is a top plan view of the portable lower back support folded for transportation and storage.
Figure 7:
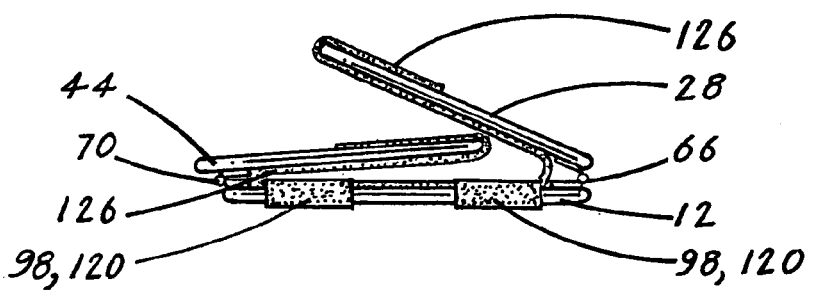
FIG. 7 is a side elevational view of the lower back support shown in a partially folded configuration.

As shown in FIGS. 6 and 7, when the horizontal rear strap 126 is loosened or released by removing one or both of the ends 136,138 or un-clasping the buckle 152, the right and left articulated sections 28,44 can be folded inward to form a flat structure. When the PLBS 10 is folded flat, transportation and storage is much easier.

While the invention has been described in complete detail and pictorially shown in the accompanying drawings it is not to be limited to such details, since many changes and modifications may be made to the invention without departing from the spirit and the scope thereof. For example, although the vertical length of the back support is dimensioned to primarily support the lower back, the vertical dimensions can be extended to support the entire back. Hence, it is described to cover any and all modifications and forms which may come within the language and scope of the claims.

What is claimed is:

1. A portable lower back support adapted to be placed upon a chair's sitting surface, adjacent the chair back's lower section, wherein said portable back support comprises:
   a) a center section having a front surface, a rear surface, an upper edge, a lower edge, a right edge and a left edge,
   b) a right articulated section having a front surface, a rear surface, an upper edge, a lower edge, a right edge and a left edge,
   c) a left articulated section having a front surface, a rear surface, an upper edge, a lower edge, a right edge and a left edge,
   d) means for attaching the left edge of said right articulated section to the right edge of said center section,
   e) means for attaching the right edge of said left articulated section to the left edge of said center section,
   f) a horizontal front support having a front surface, a rear surface, an upper edge, a lower edge, a first end and a second end,
   g) a vertical front support having a front surface, a rear surface, a right edge, a left edge, a first end and a second end,
   h) a horizontal rear strap having a front surface, a rear surface, an upper edge, a lower edge, a first end and a second end,
   i) means for attaching the first end of said horizontal front support to the rear surface of said right articulated section, and the second end to the rear surface of said left articulated section,
   j) means for attaching the first and second ends of said vertical front support to the rear surface of said center section, and
   k) means for attaching the first end of said horizontal rear strap to the front surface of said right articulated section, and the second end to the front surface of said left articulated section.

2. The portable lower back support as specified in claim 1 wherein said center, right articulated and left articulated sections are made of high-impact plastic.

3. The portable lower back support as specified in claim 2 wherein said center, right articulated and left articulated sections that are made high impact plastic further comprise a perimeter flange that provides additional structural integrity.

4. The portable lower back support as specified in claim 1 wherein said center, right articulated and left articulated sections are made of a metal with aluminum preferred.

5. The portable lower back support as specified in claim 4 wherein said center, right articulated and left articulated sections that are made of metal further comprise a perimeter flange that provides additional structural integrity.

6. The portable lower back support as specified in claim 1 wherein said attachment means for attaching the left edge of said right articulated section to the right edge of said center section, and the right edge of said left articulated section to the left edge of said center section is comprised of at least one hinge.

7. The portable lower back support as specified in claim 5 wherein said at least one hinge is comprised of a utility hinge.

8. The portable lower back support as specified in claim 5 wherein said at least one hinge is comprised a living hinge.

9. The portable lower back support as specified in claim 1 wherein said means for attaching the first end of said horizontal front support to the rear surface of said right articulated section, and the second end to the rear surface of said left articulated section is comprised of an adhesive.

10. The portable lower back support as specified in claim 1 wherein said horizontal front support is comprised of at least one horizontal front strap.

11. The portable lower back support as specified in claim 1 wherein said attachment means for attaching the first and second ends of the vertical front support to the rear surface of said center section is comprised of an adhesive.

12. The portable lower back support as specified in claim 1 wherein said vertical front support is comprised of at least one vertical strap.

13. The portable lower back support as specified in claim 1 wherein said means for attaching the first end of the horizontal rear strap to the front surface of said right articulated section, and the second end to the front surface of said left articulated section is comprised of a hook and loop fastener.

14. The portable lower back support as specified in claim 1 wherein said horizontal front support and said at least one vertical front support have a width ranging between 2 to 6 inches.

15. The portable lower back support as specified in claim 10 wherein said at least one horizontal front strap comprises two slits, with one slit located at the right edge of said right articulated section, and the other slit located at the left edge of said left articulated section, for allowing the horizontal rear strap to pass therethrough.

16. The portable lower back support as specified in claim 1 wherein when said horizontal rear strap is loosened said right and left articulated sections can be folded inward to form a flat structure for transportation or storage.

17. A portable lower back support adapted to be placed upon a chair's sitting surface, adjacent the chair back's lower section, said portable back support comprising:
   a) a center section having a front surface, a rear surface, an upper edge, a lower edge, a right edge and a left edge,
   b) a right articulated section having a front surface, a rear surface, an upper edge, a lower edge, a right edge and a left edge,
   c) a left articulated section having a front surface, a rear surface, an upper edge, a lower edge, a right edge and a left edge,
   d) means for attaching the left edge of said right articulated section to the right edge of said center section,
   e) means for attaching the right edge of said left articulated section to the left edge of said center section,
   f) a pair of spaced-apart horizontal front straps, wherein each said strap has a front surface, a rear surface, an upper edge, a lower edge, a first end and a second end, wherein the first and the second ends are attached, by an attachment means, respectively to the rear surfaces of said right and left articulated sections,
   g) a pair of spaced-apart vertical front straps, wherein each said strap has a front surface, a rear surface, an upper edge, a lower edge, a first end and a second end, wherein the first and second ends are attached, by an attachment means, respectively to the rear surface of said center section, and
   h) a horizontal rear strap having a front surface, a rear surface, an upper edge, a lower edge, a first end and a second end, wherein the first and second ends are attached, by an attachment means, respectively to the front surface of said right articulated section and to the front surface of said left articulated section, wherein said horizontal rear strap maintains said right and left articulated sections at their extended angular positions.

18. The portable lower back support as specified in claim 17, wherein said center section, said right articulated section and said left articulated section are made of aluminum having a perimeter flange that provides additional structural integrity.

19. The portable lower back support as specified in claim 17 wherein said pair of vertical front straps are attached by an attachment means to said pair of horizontal front straps.

20. The portable lower back support as specified in claim 17 wherein said horizontal rear strap further comprises a slide release buckle located where said horizontal rear strap crosses over the rear surface of said center section.

21. The portable lower back support as specified in claim 17 wherein when said horizontal rear strap is loosened said right and left articulated sections can be folded inward to form a flat structure for transportation or storage.

22. The portable lower back support as specified in claim 17 wherein said center section, said right articulated section and said left articulated section can be designed with a vertical length that supports the lower back or the vertical length can be extended to support the entire back.

* * * * *